United States Patent
Wang et al.

(10) Patent No.: US 9,757,085 B2
(45) Date of Patent: Sep. 12, 2017

(54) METHOD FOR IDENTIFYING AND PROCESSING DETECTOR POLARIZATION IN PHOTON-COUNTING SPECTRAL X-RAY DETECTORS

(71) Applicant: TOSHIBA MEDICAL SYSTEMS CORPORATION, Otawara-Shi (JP)

(72) Inventors: Xiaolan Wang, Buffalo Grove, IL (US); Yuexing Zhang, Naperville, IL (US); Yu Zou, Naperville, IL (US)

(73) Assignee: Toshiba Medical Systems Corporation, Otawara-Shi (JP)

( * ) Notice: Subject to any disclaimer, the term of this patent is extended or adjusted under 35 U.S.C. 154(b) by 262 days.

(21) Appl. No.: 14/631,519

(22) Filed: Feb. 25, 2015

(65) Prior Publication Data
US 2016/0242725 A1  Aug. 25, 2016

(51) Int. Cl.
*A61B 6/03* (2006.01)
*A61B 6/00* (2006.01)
*G06T 11/00* (2006.01)

(52) U.S. Cl.
CPC .......... *A61B 6/5258* (2013.01); *A61B 6/032* (2013.01); *A61B 6/035* (2013.01); *A61B 6/42* (2013.01); *A61B 6/4208* (2013.01); *A61B 6/4233* (2013.01); *A61B 6/4241* (2013.01); *A61B 6/4266* (2013.01); *G06T 11/003* (2013.01); *A61B 6/4435* (2013.01); *A61B 6/482* (2013.01); *A61B 6/5282* (2013.01)

(58) Field of Classification Search
CPC .......... A61B 6/032; A61B 6/035; A61B 6/42; A61B 6/4208; A61B 6/4233; A61B 6/4241; A61B 6/4266; A61B 6/4435; A61B 6/482; A61B 6/5258; A61B 6/5282
USPC ........................................ 378/19; 250/370.09
See application file for complete search history.

(56) References Cited

U.S. PATENT DOCUMENTS

| | | | | |
|---|---|---|---|---|
| 7,532,703 | B2 * | 5/2009 | Du | A61B 6/032 378/116 |
| 7,613,274 | B2 * | 11/2009 | Tkaczyk | A61B 6/032 378/19 |
| 7,652,258 | B2 * | 1/2010 | Shahar | G01T 1/24 250/370.01 |
| 7,705,319 | B2 * | 4/2010 | Bale | G01T 1/24 250/338.4 |

(Continued)

OTHER PUBLICATIONS

Derek S. Bale, et al., "Nature of Polarization in Wide-Bandgap Semiconductor Detectors Under High-Flux Irradiation: Application to Semi-Insulating $Cd_{1-x}Zn_xTe$," The American Physical Society, Physical Review B 77, 035205, Jan. 14, 2008.

*Primary Examiner* — Allen C. Ho
(74) *Attorney, Agent, or Firm* — Oblon, McClelland, Maier & Neustadt, L.L.P.

(57) ABSTRACT

A computed tomography (CT) apparatus and a method for identifying photon-counting detectors that are polarized due to high flux, thereby rendering the photon-counting detector inoperable. The data obtained from the photon-counting detectors that are determined to be polarized is skipped during an image pre-reconstruction phase. The data is further assigned a weight of zero during an image reconstruction phase in order to avoid imaging artifacts in the reconstructed CT image.

20 Claims, 8 Drawing Sheets

(56) References Cited

U.S. PATENT DOCUMENTS

| | | | | |
|---|---|---|---|---|
| 7,864,917 B2* | 1/2011 | Ribbing | ............... | A61B 6/032 378/10 |
| 7,916,836 B2* | 3/2011 | Tkaczyk | ............... | G01T 1/24 250/370.09 |
| 8,084,746 B2* | 12/2011 | Kim | ............... | G01T 1/2928 250/370.1 |
| 8,917,811 B2* | 12/2014 | Zhang | ............... | G01T 7/005 378/16 |
| 9,020,092 B2* | 4/2015 | Wang | ............... | A61B 6/583 378/5 |
| 9,101,273 B2* | 8/2015 | Gagnon | ............... | G01T 1/24 |
| 9,119,589 B2* | 9/2015 | Zou | ............... | A61B 6/032 |
| 9,155,515 B2* | 10/2015 | Petschke | ............... | A61B 6/032 |
| 9,155,516 B2* | 10/2015 | Wang | ............... | A61B 6/4241 |
| 9,198,632 B2* | 12/2015 | Zhang | ............... | A61B 6/5282 |
| 9,219,178 B2* | 12/2015 | Zhang | ............... | H01L 31/02327 |
| 9,256,938 B2* | 2/2016 | Petschke | ............... | G06T 7/0012 |
| 9,274,066 B2* | 3/2016 | Ji | ............... | G01N 23/046 |
| 9,292,946 B2* | 3/2016 | Zou | ............... | G06T 11/006 |
| 9,345,445 B2* | 5/2016 | Petschke | ............... | A61B 6/584 |
| 9,449,385 B2* | 9/2016 | Petschke | ............... | G06T 7/0012 |
| 9,462,983 B2* | 10/2016 | Zhang | ............... | A61B 6/4241 |
| 9,476,993 B2* | 10/2016 | Wang | ............... | G01T 1/17 |
| 9,482,630 B2* | 11/2016 | Wang | ............... | G01N 23/046 |
| 9,510,792 B2* | 12/2016 | Wang | ............... | A61B 6/032 |
| 9,535,174 B2* | 1/2017 | Engel | ............... | G01T 1/241 |
| 9,554,760 B2* | 1/2017 | Rodrigues | ............... | A61B 6/4241 |
| 9,618,633 B2* | 4/2017 | Rodrigues | ............... | G01T 1/241 |
| 2015/0178957 A1* | 6/2015 | Zou | ............... | A61B 6/482 382/131 |

\* cited by examiner

METHOD FOR IDENTIFYING AND PROCESSING DETECTOR POLARIZATION IN PHOTON-COUNTING SPECTRAL X-RAY DETECTORS

FIELD

Embodiments disclosed herein generally relate to computed tomography (CT) imaging. In particular, embodiments disclosed herein relate to a CT apparatus including a plurality of photon-counting detectors and an associated method thereof for identifying and processing polarized data in photon-counting detectors.

BACKGROUND

Computed tomography (CT) systems and methods are widely used, particularly for medical imaging and diagnosis. CT systems generally create images of one or more sectional slices through a subject's body. A radiation source, such as an X-ray tube, irradiates the body from one side. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

These conventional detectors are called energy-integrating detectors for acquiring energy integration X-ray data. Recently, photon-counting detectors are configured to acquire the spectral nature of the X-ray source rather than the energy integration nature in acquiring data. To obtain the spectral nature of the transmitted X-ray data, the photon-counting detectors split the X-ray beam into its component energies or spectrum bins and count a number of photons in each of the bins. The use of the spectral nature of the X-ray source in CT is often referred to as spectral CT. Since spectral CT involves the detection of transmitted X-rays at two or more energy levels, spectral CT generally includes dual-energy CT by definition.

The photon-counting detectors may include semiconductor-based CZT or CdTe sensors that have fast electronic readout capability. Semiconductor-based photon-counting detectors used in spectral CT can detect incident photons and measure photon energy for every event. However, at high flux, the CZT or CdTe sensors polarize and thereby stop functioning accurately. The information captured by the polarized sensors is severely distorted and thus is unusable. Utilizing such unusable data during image pre-reconstruction and reconstruction processing phases results in artifacts in the reconstructed CT image. Accordingly, it is essential to identify polarized detector data and process it in an appropriate manner.

BRIEF DESCRIPTION OF THE DRAWINGS

A more complete appreciation of the teachings of this disclosure and many of the attendant advantages thereof will be readily obtained as the same becomes better understood by reference to the following detailed description when considered in connection with the accompanying drawings, wherein.

DETAILED DESCRIPTION

Embodiments described herein are directed to a CT apparatus and a method thereof for identifying polarized detector data. The CT apparatus may include a plurality of fourth-generation photon-counting detectors or may include a combination of sparsely placed stationary fourth-generation detectors along with a rotating third-generation source and detector. The identified polarized detector data is excluded from the pre-processing and image reconstruction stages thereby reducing imaging artifacts.

According to one embodiment there is provided a computed-tomography (CT) apparatus that includes a plurality of stationary photon-counting detectors configured to capture incident X-ray photons emitted from an X-ray source to obtain projection data; and a processing circuit configured to determine which photon-counting detectors of the plurality of photon-counting detectors were polarized when the projection data was obtained, and assign a weight of zero to the projection data corresponding to the polarized photon-counting detectors during image reconstruction.

According to another embodiment, there is provided a method that includes: capturing, by a plurality of photon-counting detectors, incident X-ray photons emitted from an X-ray source to obtain projection data; determining, by a processing circuit, which photon-counting detectors of the plurality of photon-counting detectors were polarized when the projection data was obtained; and assigning a weight of zero to the projection data corresponding to the polarized photon-counting detectors during image reconstruction.

In another embodiment, there is provided a non-transitory computer readable medium having stored thereon a program that when executed by a computer, causes the computer to execute a method, the method includes the steps of: capturing, by a plurality of photon-counting detectors, incident X-ray photons emitted from an X-ray source to obtain projection data; determining, by a processing circuit, which photon-counting detectors of the plurality of photon-counting detectors were polarized when the projection data was obtained; and assigning a weight of zero to the projection data corresponding to the polarized photon-counting detectors during image reconstruction.

Figure 1:
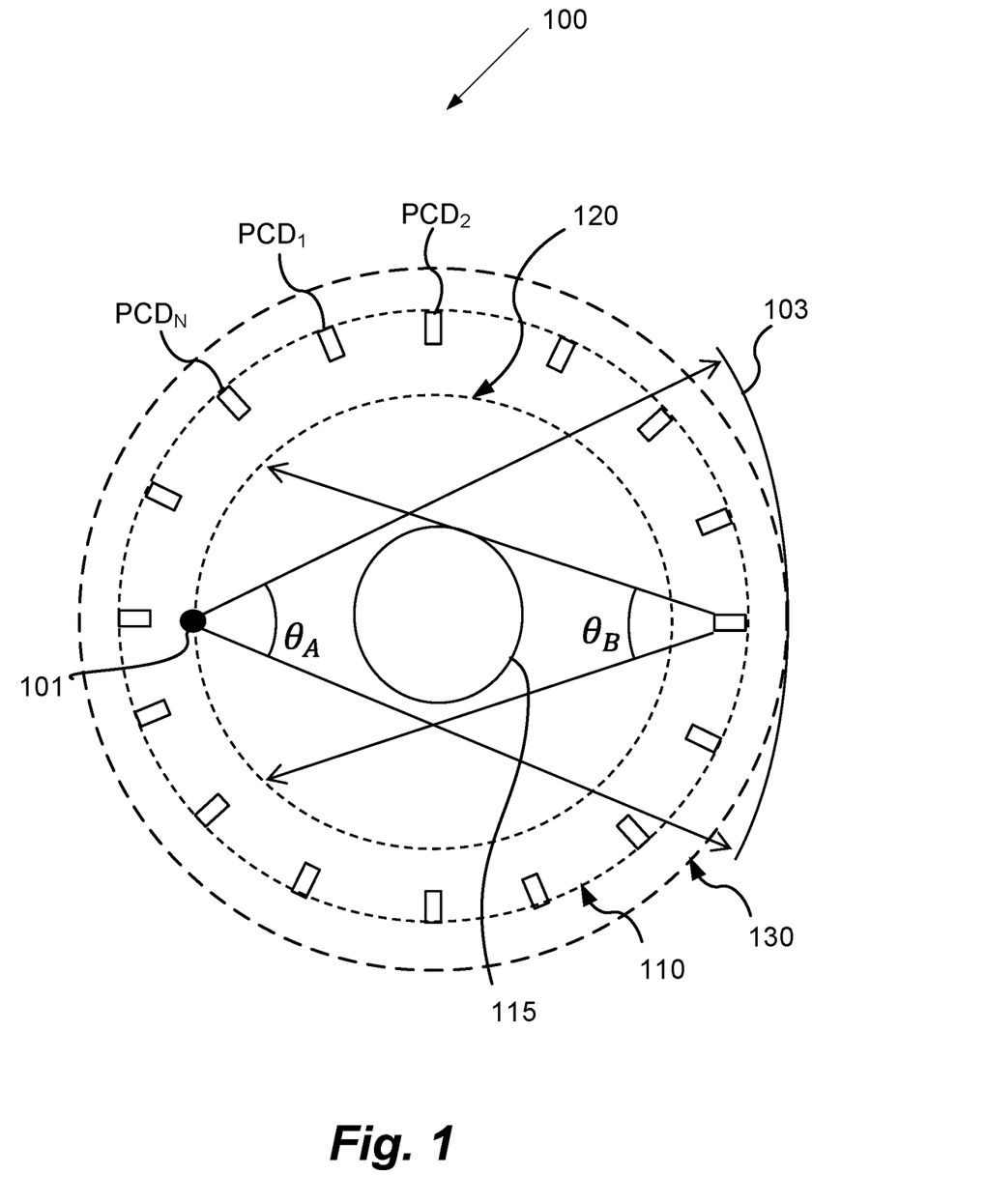
FIG. 1 shows a diagram of a cross-section of a combined third-generation and fourth-generation computed tomography apparatus.

Referring now to the drawings, wherein like reference numerals designate identical or corresponding parts throughout the several views, FIG. 1 shows a diagram illustrating an implementation for placing the photon-counting detectors (PCDs) in a predetermined fourth-generation geometry in combination with a detector unit in a predetermined third-generation geometry in a CT scanner system.

The diagram illustrates relative positions among an object 115 to be scanned, an X-ray source 101, an X-ray detector 103, and the photon-counting detectors $PCD_1$ through $PCD_N$ in one exemplary embodiment. For the sake of simplicity, the diagram excludes other components and circuitry necessary in acquiring and processing data and reconstructing an image based upon the acquired data. In general, the photon-counting detectors $PCD_1$ through $PCD_N$ each output a photon count for each predetermined energy bin. In addition to the sparse photon-counting detectors $PCD_1$ through $PCD_N$ in the fourth-generation geometry, the implementation shown in FIG. 1 includes a detector unit such as the detector 103 in conventional third-generation geometry in the CT scanner system. The detector elements in the detector unit 103 are more densely placed along the detector unit surface than the photon-counting detectors $PCD_1$ through $PCD_N$.

In one implementation, the photon-counting detectors $PCD_1$ through $PCD_N$ are sparsely placed around the object 115 in a predetermined geometry, such as a circle. For example, the photon-counting detectors $PCD_1$ through $PCD_N$ are fixedly placed on a predetermined circular component 110 in the gantry 100. In one implementation, the photon-counting detectors $PCD_1$ through $PCD_N$ are fixedly placed on the circular component 110 at predetermined equidistant positions. In an alternative implementation, the photon-counting detectors $PCD_1$ through $PCD_N$ are fixedly placed on the circular component 110 at predetermined non-equidistant positions. The circular component 110 remains stationary with respect to the object 115 and does not rotate during the data acquisition. Both the X-ray source 101 and the detector unit 103 rotate around the object 115 while the photon-counting detectors $PCD_1$ through $PCD_N$ are stationary with respect to the object 115.

In one implementation, the X-ray source 101 is mounted on a first rotating portion 120 such as the annular frame in the gantry 100 so that the X-ray source 101 projects X-ray radiation with a predetermined source fan beam angle $\theta_A$ towards the object 115 while the X-ray source 101 rotates around the object 115 inside the sparsely placed photon-counting detectors $PCD_1$ through $PCD_N$. Furthermore, an additional detector unit 103 is mounted on a second rotating portion 130 in the third-generation geometry. The second rotating portion 130 mounts the detector unit 103 at a diametrically opposed position from the X-ray source 101 across the object 115 and rotates outside the stationary circular component 110, on which the photon-counting detectors $PCD_1$ through $PCD_N$ are fixedly placed in a predetermined sparse manner.

In one implementation, the first rotating portion 120 and the second rotating portion 130 are integrally constructed as a single component, such as the annular frame, to maintain a 180-degree angle between the X-ray source 101 and the detector unit 103 as they rotate about the object 115 with a different radius. In an optional implementation, the first rotating portion 120 and the second rotating portion 130 are separate components, but synchronously rotate to maintain the X-ray source 101 and the detector unit 103 in the fixedly opposed positions at 180 degrees across the object 115. Furthermore, in an alternate implementation, both the X-ray source 101 and the third generation detector unit 103 traverse a helical path, wherein the detector unit 103 is positioned directly opposite the X-ray source 101, as the object 115 is moved in a predetermined direction that is perpendicular to the rotational plane of the first rotating portion 120.

As the X-ray source 101 and the detector unit 103 rotate around the object 115, the photon-counting detectors PCDs and the detector unit 103 respectively detect the transmitted X-ray radiation during data acquisition. The photon-counting detectors $PCD_1$ through $PCD_N$ intermittently detect, for a predetermined detector fan beam angle $\theta_B$ the X-ray radiation that has been transmitted through the object 115 and individually output a count value representing a number of photons, for each of predetermined energy bins. On the other hand, the detector elements in the detector unit 103 continuously detect the X-ray radiation that has been transmitted through the object 115 and output the detected signals as the detector unit 103 rotates. In one implementation, the detector unit 103 has densely placed energy-integrating detectors in predetermined channel and segment directions on the detector unit surface.

In one implementation, the X-ray source 101, the photon-counting detectors $PCD_1$ through $PCD_N$ and the detector unit 103 collectively form three predetermined circular paths that differ in radius. The photon-counting detectors $PCD_1$ through $PCD_N$ are sparsely placed along a first circular path around the object 115 while at least one X-ray source 101 rotates along a second circular path around the object 115. Further, the detector unit 103 travels along a third circular path. The above exemplary embodiment illustrates that the third circular path is the largest and outside the first and second circular paths around the object 115. Although not illustrated, an alternative embodiment optionally changes the relative relation of the first and second circular paths so that the second circular path for the X-ray source 101 is larger and outside the first circular path of the sparsely placed photon-counting detectors $PCD_1$ through $PCD_N$ around the object 115. Furthermore, in another alternative embodiment, the X-ray source 101 also optionally travels on the same third circular path as the detector unit 103. Furthermore, the above alternative embodiments optionally provide a protective rear cover for each of the photon-counting detectors $PCD_1$ through $PCD_N$ that are irradiated from behind at a short distance as the X-ray source 101 travels outside the first circular path of the sparsely placed photon-counting detectors $PCD_1$ through $PCD_N$.

There are other alternative embodiments for placing the photon-counting detectors $PCD_1$ through $PCD_N$ in predetermined fourth-generation geometry in combination with the detector unit 103 in the predete lined third-generation geometry in the CT scanner. The X-ray source 101 is optionally a single-energy source in certain embodiments. By the same token, an additional alternative embodiment optionally includes the X-ray source 101, which is configured to perform a kV-switching function for emitting X-ray radiation at a predetermined high-level energy and at a predetermined low-level enemy.

In general, the photon-counting detectors $PCD_1$ through $PCD_N$ are sparsely positioned along the circular component 110. Although the photon-counting detectors $PCD_1$ through $PCD_N$ acquire sparse view projection data, the acquired projection data is sufficient for at least dual-energy (DE) reconstruction with a sparse view reconstruction technique. In addition, the detector unit 103 also acquires another set of projection data, and the projection data from the detector unit 103 is used to generally improve image quality. In case that the detector unit 103 includes energy-integrating detectors with anti-scatter grids, the projection data from the detector unit 103 is used to correct scatter on the projection data from the photon-counting detectors. In one implementation, the energy integrating detectors optionally need to be calibrated in view of X-ray transmission through the predetermined circular component 110 and some of the photon-counting detectors $PCD_1$ through $PCD_N$.

Figure 2:
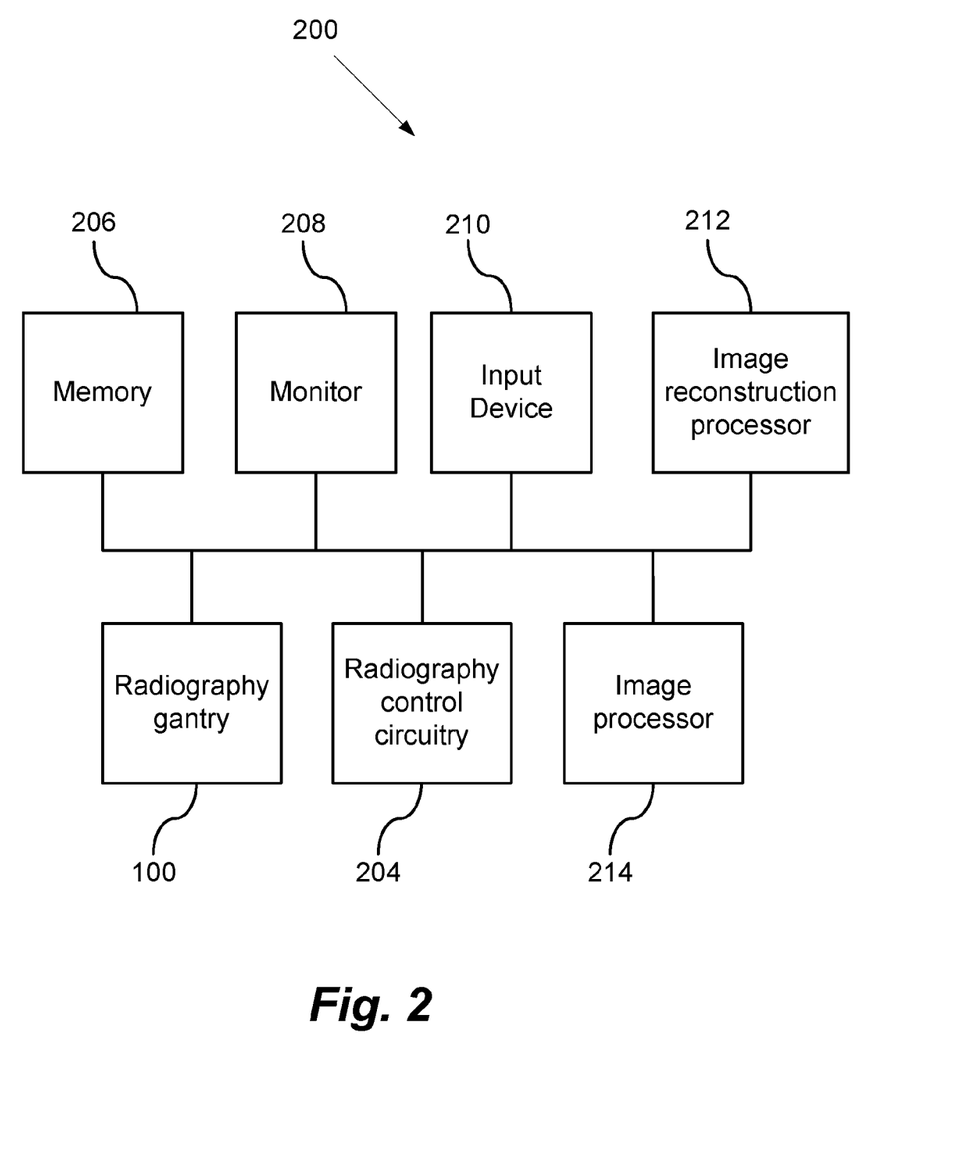
FIG. 2 shows a schematic of a computed tomography system.

FIG. 2 shows a schematic of an X-ray CT scanner system 200. The X-ray CT scanner system 200 comprises a radiography gantry 100, radiography control circuitry 204, memory 206, monitor 208, input device 210, image reconstruction processor 212, and image processor 214. The radiography control circuitry 204 controls the rotation of the CT gantry 100, the application of high voltages from a high voltage generator to the X-ray source 101, and the reading of signals from the detector unit 103 in order to execute rotational radiography and generate CT projection data. The memory 206 stores a dedicated program for executing a combined third-generation and fourth-generation image reconstruction method. The monitor 208 is a display device such as a CRT, plasma display, or liquid crystal display which displays an X-ray diagnostic imaae in a predetermined form in accordance with a signal received from the image reconstruction processor 212 or the image processor 214. The input device 210 includes a keyboard, various kinds of switches, a mouse, etc. and is used to input a radiography instruction, image selection instruction, etc. The image reconstruction processor 212 reconstructs volume data from projection images in a plurality of projection directions. The image processor 214 executes predetermined image processing such as volume rendering processing and image difference processing as needed.

A major problem encountered by photon-counting detectors $PCD_1$ through $PCD_N$ is the possible inoperability of the semiconductor sensors under high X-ray flux. High X-ray flux that is commonly encountered in CT scans and causes the CdTe/CdZnTe sensors to "polarize" and stop functioning.

Polarization may further occur when the incident rays of photons are not perpendicular to a top face of the detector element (DE). When the photons enter through the side face, the geometrical efficiency of the DE is different from the case of normal incidence through the top face. Photons entering the DE from different locations, e.g., the top face and the side face, travel different distances through the DE, which causes photons in different rays to have different energy response, and different detection efficiency, etc.

During polarization, the detector element (DE) output is not zero, but the captured information is severely distorted and no longer usable. Thus, if the polarization in the detector element (DE) output is not accurately identified, the unusable data propagates through a pre-reconstruction process, as well as during the image reconstruction, e.g., in the iterative reconstruction (IR) stage, to the image domain, thereby resulting in imaging artifacts.

Figure 3:
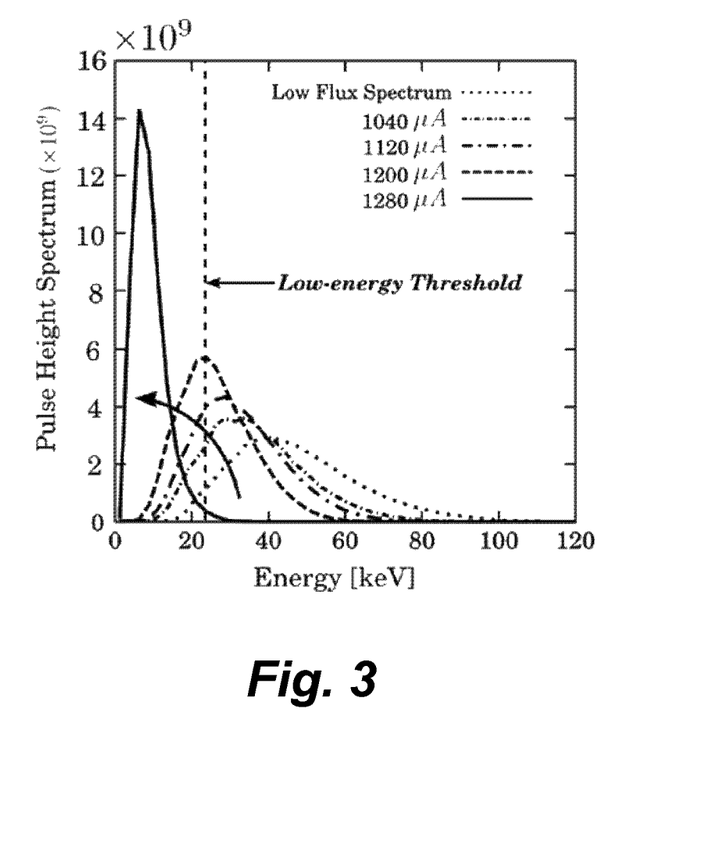
FIG. 3 depicts, according to a non-limiting example, X-ray spectrum obtained from polarized data.

For instance, FIG. 3 depicts, according to a non-limiting example, X-ray spectra obtained at different incident X-ray fluxes. FIG. 3 illustrates the height of the spectrum (plotted on the Y-axis) against energy (plotted on the X-axis). The effect of polarization in the photon-counting detectors tends to collapse (i.e., shift) the spectrum towards low energy. Specifically, during polarization a space charge builds up in the photon-counting detector that prevents the signal from being measured accurately. Accordingly, it is essential to identify polarized detector data, and consequently, exclude the usage of the polarized data in CT image reconstruction.

Figure 4:
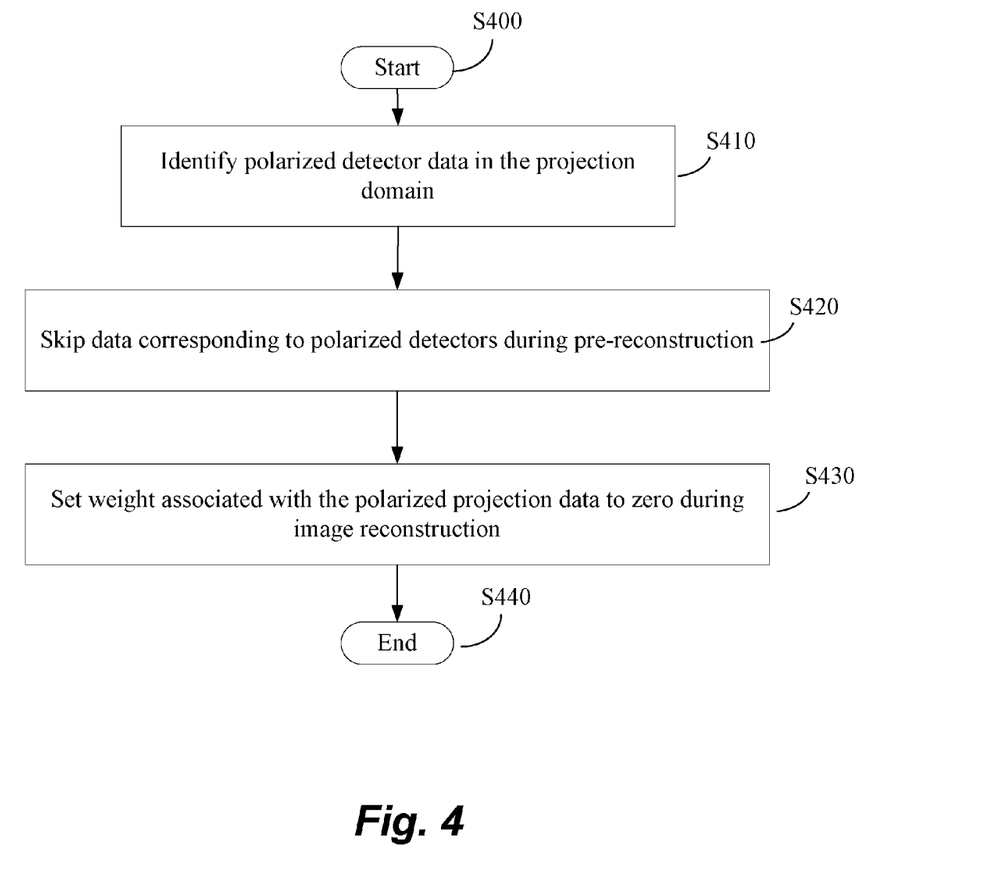
FIG. 4 illustrates a flowchart depicting the steps performed to identify and process polarized data.

FIG. 4 illustrates, according to one embodiment, a flowchart depicting the steps performed to process polarized data.

The process starts in step S400 and proceeds to step S410. In step S410, the data corresponding to the polarized photon-counting detectors is identified. Specific techniques describing the methods to identify the polarized photon-counting detector data are described later with reference to FIGS. 5A and 5B.

The process then proceeds to step S420, wherein the identified polarized data corresponding to the polarized photon-counting detectors is skipped during an image pre-reconstruction stage. In the pre-reconstruction stage, processing circuitry of the CT system performs pre-reconstruction by correcting a sinogram (a 2-D array of data containing the projections) for scatter and pileup effects, and performs material decomposition in the projection domain, based on a verified kV-waveform and calibrated beam-hardening tables. For every ray, the scanned spectral data from a photon-counting detector is corrected for scatter and pileup, weighted for noise balance, and decomposed into basis materials.

Furthermore, while performing image reconstruction, a weight is associated with each element of projection data that is used for image reconstruction. Image reconstruction techniques such as iterative image reconstruction, typically start with an assumed image, and compute projections from the image. Further, an iterative reconstruction algorithm typically updates the image based upon the difference between the calculated and the actual projections, in order to construct the final image. Accordingly, the process in step S430, assigns a weight of zero to the polarized data projections so that those projections are not taken into account while reconstructing the image, (i.e., the projections do not impact the quality of the final image), whereafter the process of FIG. 4 terminates in step S440.

Figure 5A:
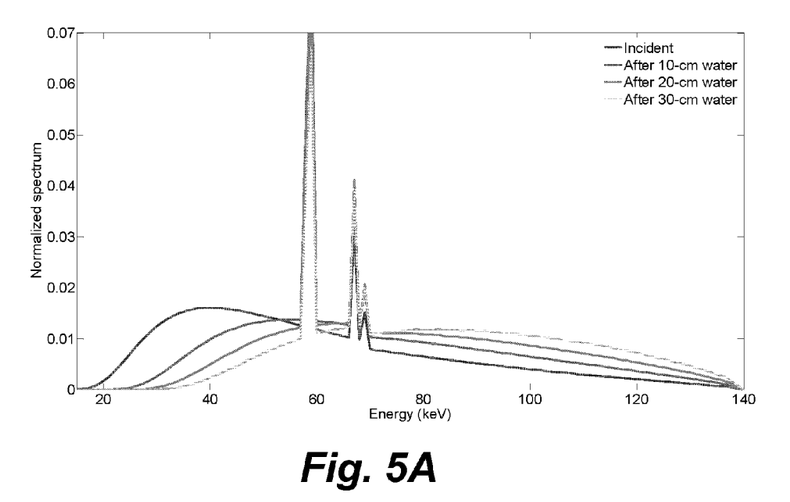
FIG. 5A illustrates spectra obtained after X-ray attenuation through an object and FIG. 5B depicts an example illustrating computation of angular separation for a given spatial resolution.

FIG. 5A illustrates, according to one embodiment, the basis for a technique for identifying polarized detector data. FIG. 5A depicts an X-ray spectrum after it is attenuated by different thickness of water. The object attenuation incurred during a CT scan tends to shift the spectrum towards higher energies. With this in mind, one method of identifying polarized photon-counting detectors (and thus correspondingly, polarized detector data) is to set a beam-hardness threshold. According to an embodiment, the threshold is based on an average energy of the spectrum or alternatively may be based on a ratio of the counts of high energy to the counts of low energy. The data with spectrum average energy or count ratio below the threshold is determined to be data from polarized photon-counting detectors, while otherwise the data is determined to be data that is useful for image reconstruction. In an alternative implementation, the average energy or count ratio of the before-object incident spectrum (known to the manufacturer) may be used as a threshold. Specifically, the average energy/counts ratio of the incident curve in FIG. 5A can be used as the threshold.

According to another embodiment, the polarized data of the photon-counting detectors is determined based on a number of adjacent views ('T') of the CT system that satisfy a particular criterion. According to Beer's law, it is known that, as the number of counts reduces, the corresponding spectrum is hardened, i.e., the spectrum tends to shift towards higher energies. In contrast, a higher number of counts (i.e., high flux) tends to soften the spectrum (i.e., the spectrum moves towards the lower energies). Thus, a scenario wherein lower counts as well as a soft spectrum are obtained can only be attributed to the case of the photon-counting detector being polarized. Such a polarization prevents efficient collection of X-ray counts (low counts) and distorts the detected spectrum.

In order to determine the magnitude of the adjacent 'T' views, it is assumed that the attenuation path is constant within the views. Further, a count change in the views is represented as ΔN, whereas the change in energy is represented as ΔE. In order to satisfy the criteria of observing a lower count as well as a soft spectrum, both ΔN and ΔE have to be negative. Thus, for view data captured at time t1, if the data captured from t1+1 to t1+T meets the above criteria, the captured data in the adjacent 'T' views is determined to be polarized data.

Figure 5B:
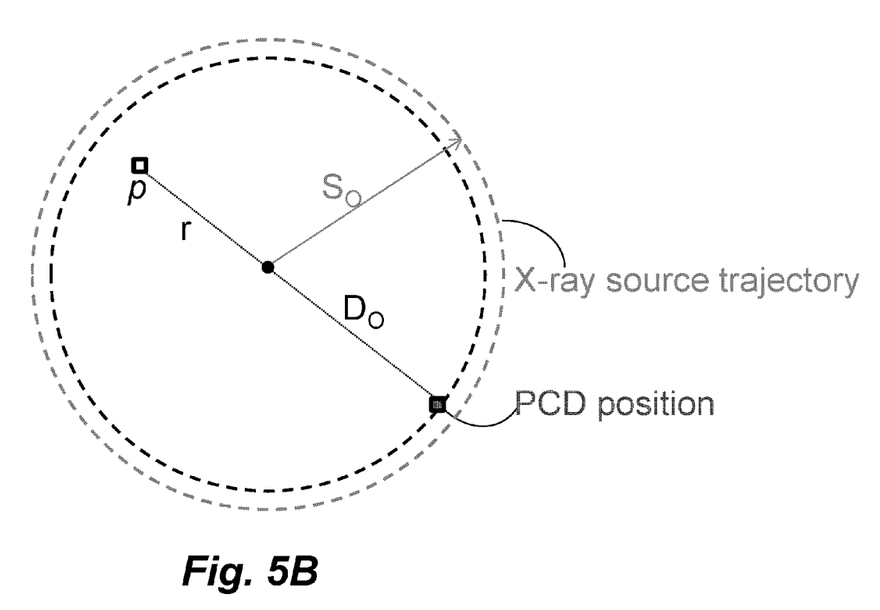

FIG. 5B depicts an example illustrating computation of an angular separation for a given spatial resolution of the CT system. The calculations enable one to compute the magnitude of the number of adjacent views 'T', such that adjacent data captured in the 'T' views can be determined to be polarized.

In FIG. 5B, an X-ray source 101 rotates on a circular trajectory that has a radial distance represented by '$S_o$' from the center of the CT gantry 100. Further the photon-counting detector is located at a radial distance represented by '$D_o$' from the center of the gantry 100. In such a setting, for a full scan that includes N views, every view covers a radial angle of 360°/N at the center. This corresponds to approximately an angle of 360°/2N at the detector surface. It must be appreciated that the exact value of the angle at the detector surface is dependent on the values of the radial distances $S_o$ and $D_o$. For a spatial resolution of the CT system represented as ρ, the angular separation at the photon-counting detector can be computed as $$\left(\sin^{-1}\frac{\rho}{r+D_o}\right).$$

Accordingly, the magnitude of the number of adjacent views 'T' can be computed as a ratio of the detector angle at the surface and the angular separation at the photon-counting detector. Specifically, the magnitude of 'T' can be computed as:

$$\left(\frac{360°/2N}{\sin^{-1}\frac{\rho O}{r+D}}\right).$$

According to another embodiment, the polarized photon-counting detector data may be determined for a CT system that includes a combination of sparsely placed, stationary fourth-generation photon-counting detectors and a rotating third generation X-ray source 101/detector unit 103.

Figure 6A:
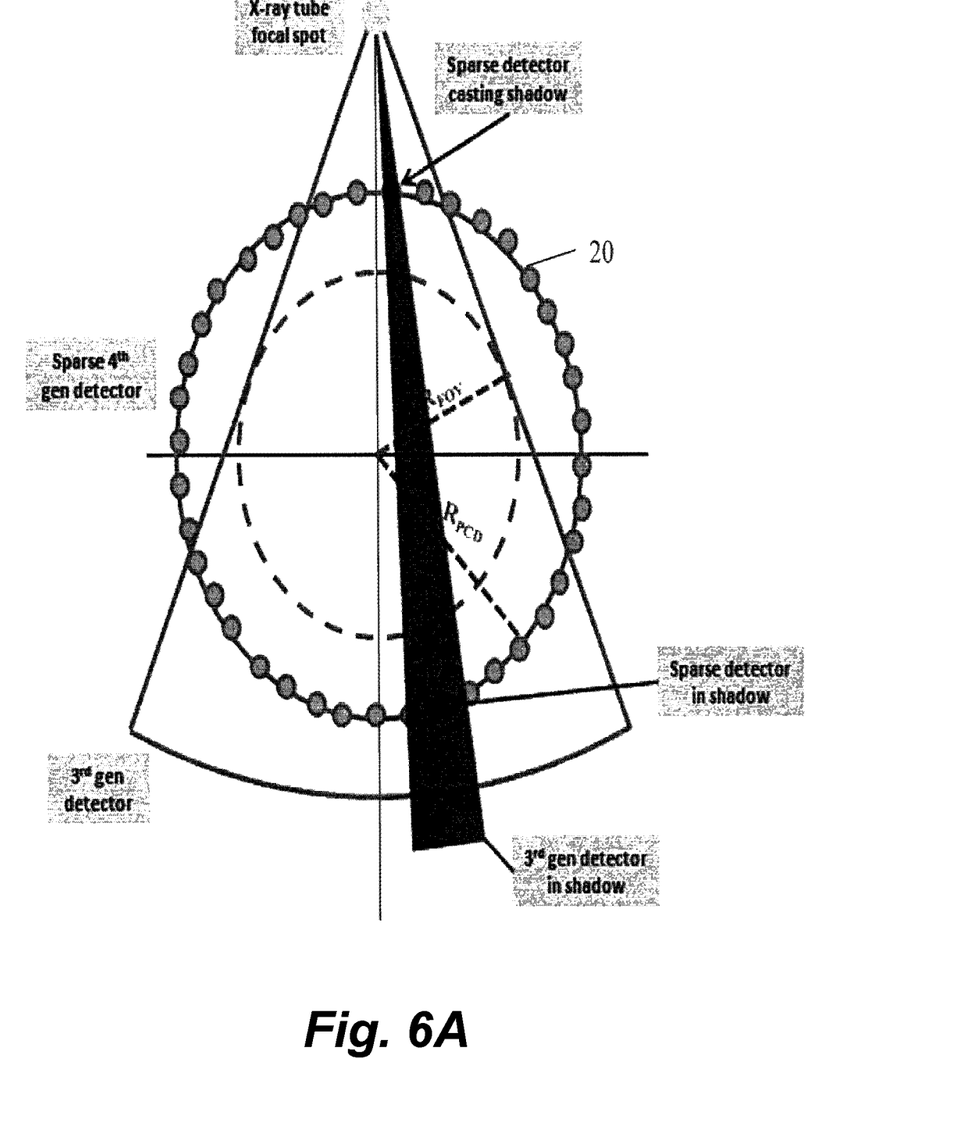
FIG. 6A illustrates, according to another embodiment, a CT scanner apparatus including fixed photon-counting detectors, a rotating X-ray source, and third generation detectors.

FIG. 6A illustrates a combined third/fourth generation system having stationary, sparsely distributed fourth-generation detectors photon-counting 20, along with a rotating third-generation X-ray source 101/detector unit 103 system. As shown in FIG. 6A, some sparse PCDs cast shadows onto other sparse PCDs and third-generation detector units. According to one embodiment, a shadow value (described below with reference to FIG. 6B) can be used to identify polarized data. Specifically, third-generation detector units that are identified to be either fully or partially under a shadow will not be used to perform detection of polarization since the detector units under shadow do not represent an accurate measurement of the actual flux.

Figure 6B:
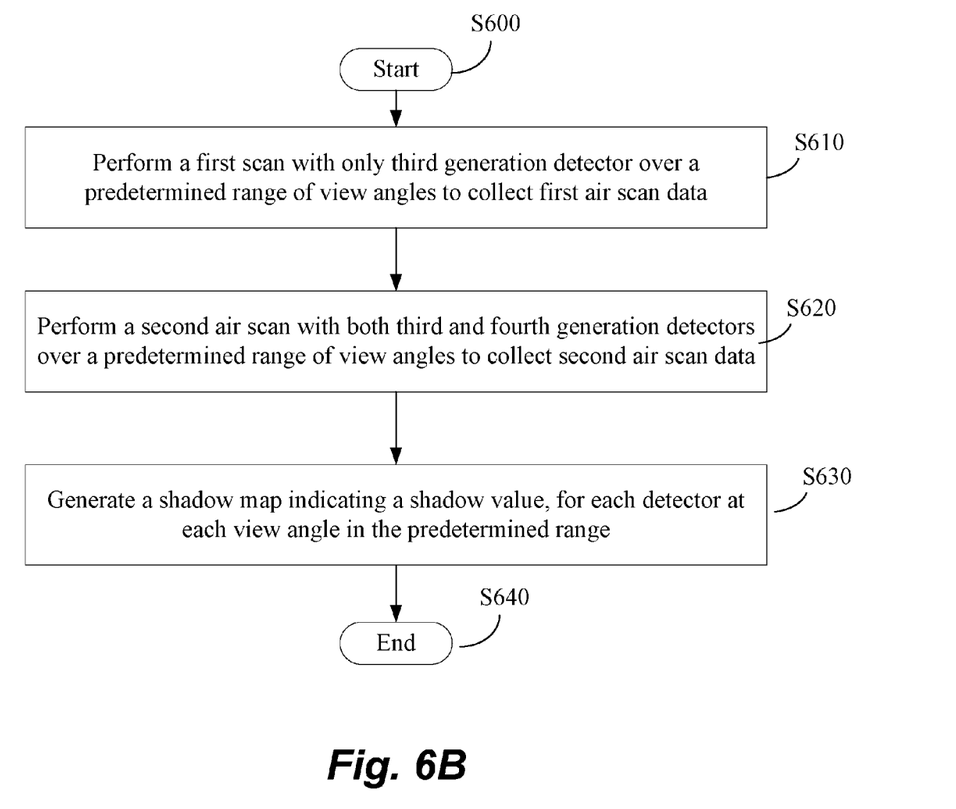
FIG. 6B illustrates a flowchart depicting the steps performed to determine a shadow value for each photon-counting detector.

FIG. 6B illustrates a flowchart for determining a shadow map for each PCD in a combined $3^{rd}/4^{th}$ generation system according to one embodiment.

The process starts in step S600 and proceeds to step S610. In step S610, an air scan is performed for the system of FIG. 6A, but with the fourth-generation photon-counting detectors removed. This initial air scan is performed for a full set of views and data is collected at each third-generation detector for each view.

In step S620, a second air scan is performed for the system of FIG. 6A, including both the third and fourth-generation detector elements. The second air scan is performed for the same set of views as performed in the initial air scan, and data is collected at each third-generation detector and at each fourth-generation photon-counting detector for each view.

In step S630, a shadow map/table is generated based on the data collected in steps S610 and S620. The shadow map includes a shadow data value for each detector element for each view. The shadow data generally indicates whether a particular detector element is in shadow for a particular view. For instance, in one embodiment, the shadow value, for each view and each detector element, is one of the following four values: (1) "off," meaning that for the given view, the given detector element is not in the field of view: (2) "not blocked," meaning that X-rays from the X-ray source are not blocked at all by any of the fourth-generation photon-counting detectors; (3) "completely blocked," meaning that all X-rays from the X-ray source are completely blocked by a fourth-generation photon-counting detector; and (4) "partially blocked," meaning that X-rays from the X-ray source are partially blocked by a fourth-generation photon-counting detector or that the given detector element is partially in shadow. Upon computing the shadow map for each detector, the process ends in step S640.

According to one embodiment, a signal threshold (M') may be predetermined such that if a third-generation detector unit detects a signal having a strength M, such that M is greater than M', then the corresponding X-ray is deemed to have a high flux. Accordingly, the fourth-generation photon-counting detector corresponding to the location of the third generation detector unit is determined to be a polarized photon-counting detector and thus the data obtained from the fourth-generation photon-counting detector is not taken into consideration during the pre-reconstruction and reconstruction stages. It must be noted that the signal detected at the third generation detector unit must be corrected for a reference detector signal. This can be achieved by using a reference detector that can be placed adjacent to the X-ray source in order to monitor source output fluctuation.

Thus, upon computing the shadow map by the method described in FIG. 6B, the shadow map is used to identify whether the signal corresponding to the third generation detector unit can be used to determine whether a fourth generation photon-counting detector is polarized. Note however that a shadowed third generation detector unit signal cannot be used to determine the polarization status of the corresponding fourth generation photon-counting detector. In such an instance, the signals received by the third generation detector unit near a shadow can be used to determine whether the fourth generation photon-counting detector, that causes the shadow, is polarized or not.

Figure 7:
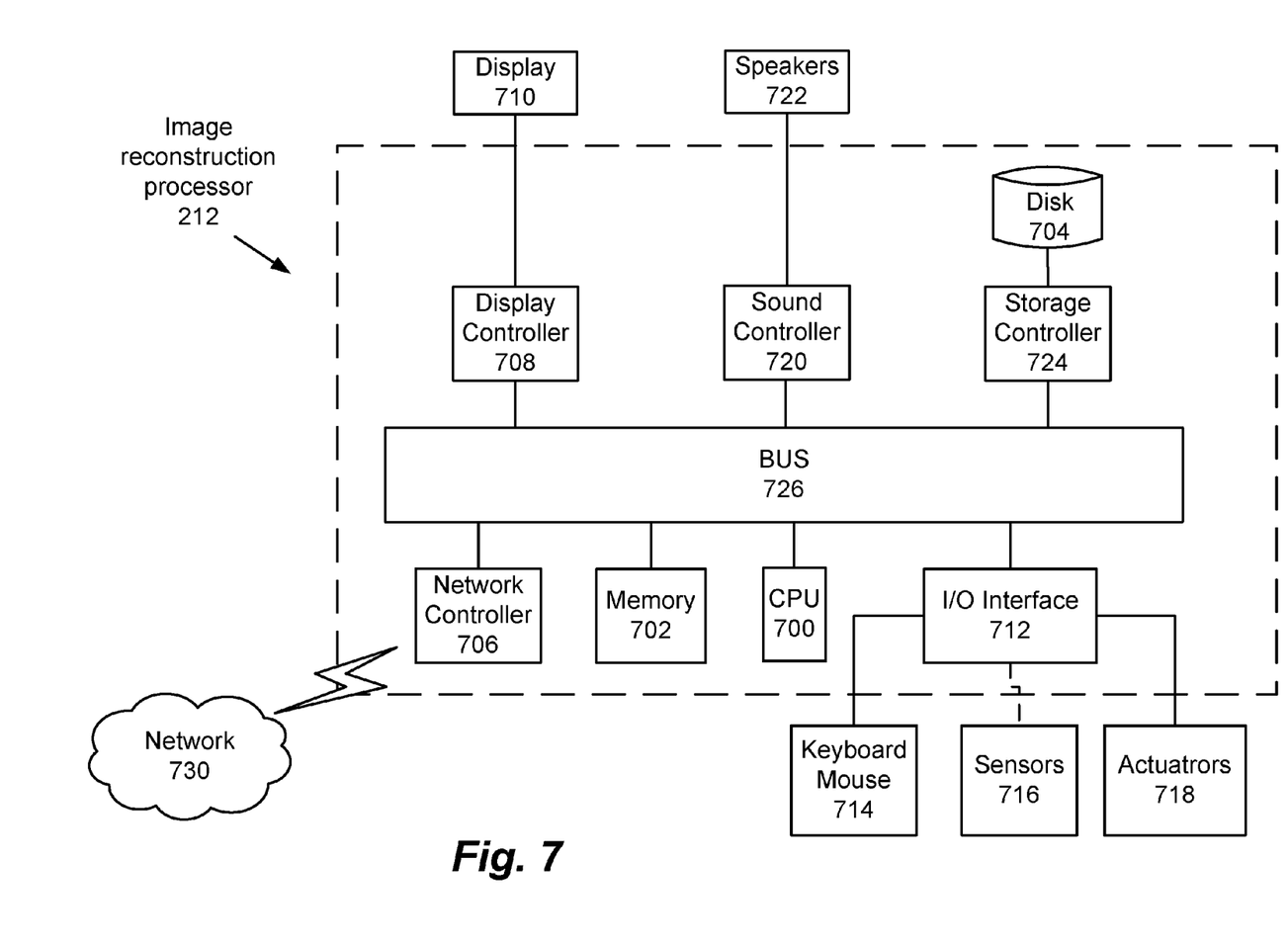
FIG. 7 shows a schematic diagram of an implementation of an image reconstruction processing unit.

FIG. 7 shows an implementation of the image reconstruction processor 212 that at least performs the methods of FIG. 4 and FIG. 6B. Next, a hardware description of the image reconstruction processor 212 according to exemplary embodiments is described with reference to FIG. 7. In FIG. 7, the image reconstruction processor 212 includes a CPU 700 which performs the processes described herein. Process data and instructions may be stored in memory 702. Processes and instructions may also be stored on a storage medium disk 704 such as a hard drive (HDD) or portable storage medium or may be stored remotely. Further, this disclosure is not limited by the form of the computer-readable media on which the instructions are stored. For example, the instructions may be stored on CDs, DVDs, in FLASH memory, RAM, ROM, PROM, EPROM, EEPROM, hard disk or any other information processing device with which the image reconstruction processor 212 communicates, such as a server or computer.

Further, aspects of this disclosure may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

CPU 700 may be a Xenon or Core processor from Intel of America or an Opteron processor from AMD of America, or may be other processor types that would be recognized by one of ordinary skill in the art, such as an ARM-based processor. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The image reconstruction processor 212 in FIG. 7 also includes a network controller 706, such as an Intel Ethernet PRO network interface card from Intel Corporation of America, for interfacing with network 730. As can be appreciated, the network 730 can be a public network, such as the Internet, or a private network such as an LAN or WAN network, or any combination thereof and can also include PSTN or ISDN sub-networks. The network 730 can also be wired, such as an Ethernet network, or can be wireless such as a cellular network including EDGE, 3G and 4G wireless cellular systems. The wireless network can also be WiFi, Bluetooth, or another wireless form of communication.

The image reconstruction processor 212 further includes a display controller 708, such as a NVIDIA GeForce GTX or Quadro graphics adaptor from NVIDIA Corporation of America that respectively interface with a corresponding display 710, such as a Hewlett Packard HPL2445w LCD monitor.

The image reconstruction processor 212 further includes a general purpose I/O interface 712 interfaces with a keyboard and/or mouse 714 as well as sensors 716. The general purpose I/O interface 712 can also connect to a variety of actuators 718. The general purpose I/O interface 712 can also connect to a variety of peripherals including printers and scanners, such as an OfficeJet or DeskJet from Hewlett Packard.

A sound controller 720 is also provided in the image reconstruction processing processor 212, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the image reconstruction processing processor 212. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, comprising:
a plurality of stationary photon-counting detectors configured to capture incident X-ray photons emitted from an X-ray source to obtain projection data; and
a processing circuit configured to
determine which photon-counting detectors of the plurality of stationary photon-counting detectors were polarized when the projection data was obtained, and
assign a weight of zero to the projection data corresponding to the polarized photon-counting detectors during image reconstruction.

2. The CT apparatus of claim 1, wherein the processing circuit is further configured to skip portions of the projection data corresponding to the polarized photon-counting detectors during pre-reconstruction processing.

3. The CT apparatus of claim 1, wherein the processing circuit is further configured to determine that a photon-counting detector of the plurality of stationary photon-counting detectors was polarized when projection data obtained from the photon-counting detector has an average energy lower than a predetermined energy threshold, wherein the predetermined energy threshold is based on an average energy of a CT spectrum.

4. The CT apparatus of claim 1, wherein the processing circuit is further configured to determine that a photon-counting detector of the plurality of stationary photon-counting detectors was polarized when projection data obtained from the photon-counting detector has an average energy lower than a predetermined energy threshold, wherein the predetermined energy threshold being based on a ratio of counts of high energy of a CT spectrum to counts of low energy of the CT spectrum.

5. The CT apparatus of claim 1, wherein the processing circuit is further configured to determine that a photon-counting detector of the plurality of stationary photon-counting detectors was polarized when a change in a number of counts and an average energy detected at the photon-counting detector is negative for a number of adjacent views of the photon-counting detector.

6. The CT apparatus of claim 5, wherein the processing circuit is further configured to determine the number of adjacent views as a ratio of a surface angle of the photon-counting detector and an angular separation of the photon-counting detector.

7. The CT apparatus of claim 1, further comprising:
an X-ray source configured to emit X-rays; and
a CT detector including a plurality of energy integrating detectors, the CT detector configured to rotate in synchronization with the X-ray source.

8. The CT apparatus of claim 7, wherein the processing circuit is further configured to determine that a photon-counting detector of the plurality of stationary photon-counting detectors is polarized when a signal strength received by the CT detector is higher than a predetermined signal threshold of the CT detector.

9. The CT apparatus of claim 7, wherein the processing circuit is further configured to determine that a photon-counting detector of the plurality of stationary photon-counting detectors is polarized based on projection data obtained by the CT detector.

10. The CT apparatus of claim 9, wherein the processing circuit is further configured to determine that, for a given detector element in the CT detector at a given view angle, the detector element is one of completely blocked, partially blocked, and not blocked.

11. A method performed by a computed-tomography (CT) apparatus, the method comprising:

capturing, by a plurality of photon-counting detectors, incident X-ray photons emitted from an X-ray source to obtain projection data;

determining, by a processing circuit, which photon-counting detectors of the plurality of photon-counting detectors were polarized when the projection data was obtained; and assigning a weight of zero to the projection data corresponding to the polarized photon-counting detectors during image reconstruction.

12. The method of claim 11, further comprising:
skipping portions of the projection data corresponding to the polarized photon-counting detectors during pre-reconstruction processing.

13. The method of claim 11, wherein the determining step comprises determining that a photon-counting detector of the plurality of photon-counting detectors was polarized when projection data obtained from the photon-counting detector has an average energy lower than a predetermined energy threshold, wherein the predetermined energy threshold is based on an average energy of a CT spectrum.

14. The method of claim 11, wherein the determining step comprises determining that a photon-counting detector of the plurality of photon-counting detectors was polarized when projection data obtained from the photon-counting detector has an average energy lower than a predetermined energy threshold, wherein the predetermined energy threshold being based on a ratio of counts of high energy of a CT spectrum to counts of low energy of the CT spectrum.

15. The method of claim 11, wherein the determining step comprises determining that a photon-counting detector of the plurality of photon-counting detectors was polarized when a change in a number of counts and an average energy detected at the photon-counting detector is negative for a number of adjacent views of the photon-counting detector.

16. The method of claim 15, wherein the determining step comprises determining the number of adjacent views as a ratio of a surface angle of the photon-counting detector and an angular separation of the photon-counting detector.

17. A non-transitory computer-readable medium having stored thereon a program that when executed by a computer causes the computer to execute a method comprising:

capturing, by a plurality of photon-counting detectors, incident X-ray photons emitted from an X-ray source to obtain projection data;

determining, by a processing circuit, which photon-counting detectors of the plurality of photon-counting detectors were polarized when the projection data was obtained; and assigning a weight of zero to the projection data corresponding to the polarized photon-counting detectors during image reconstruction.

18. The non-transitory computer readable medium of claim 17, the method further comprising:

skipping portions of the projection data corresponding to the polarized photon-counting detectors during pre-reconstruction processing.

19. The non-transitory computer readable medium of claim 17, wherein the determining step comprises determining that a photon-counting detector of the plurality of photon-counting detectors was polarized when projection data obtained from the photon-counting detector has an average energy lower than a predetermined energy threshold, wherein the predetermined energy threshold is based on an average energy of a CT spectrum.

20. The non-transitory computer readable medium of claim 17, wherein the determining step comprises determining that a photon-counting detector of the plurality of photon-counting detectors was polarized when projection data obtained from the photon-counting detector has an average energy lower than a predetermined energy threshold, wherein the predetermined energy threshold being based on a ratio of counts of high energy of a CT spectrum to counts of low energy of the CT spectrum.

* * * * *